US006620852B2

(12) United States Patent
Brogan et al.

(10) Patent No.: US 6,620,852 B2
(45) Date of Patent: Sep. 16, 2003

(54) TOPICAL ANESTHETIC

(76) Inventors: Gerald Brogan, 8 Beardsley La., Huntington, NY (US) 11743; Joel Karen, 140 Round Swamp Rd., Huntington, NY (US) 11743; Richard Malerba, 11 Beecher St., Coram, NY (US) 11727

( * ) Notice: Subject to any disclaimer, the term of this patent is extended or adjusted under 35 U.S.C. 154(b) by 0 days.

(21) Appl. No.: 10/023,423

(22) Filed: Dec. 17, 2001

(65) Prior Publication Data

US 2003/0114522 A1 Jun. 19, 2003

(51) Int. Cl.⁷ .................. A61K 31/16; A61K 31/35; A61K 31/24
(52) U.S. Cl. .................. 514/626; 514/535; 514/536; 514/960; 514/649; 514/537
(58) Field of Search .................. 514/626, 535, 514/536, 537, 649, 960, 930

(56) References Cited

U.S. PATENT DOCUMENTS

| 5,563,153 A | * | 10/1996 | Mueller et al. | 514/305 |
| 5,708,031 A | * | 1/1998 | Scott | 514/573 |
| 5,840,755 A | * | 11/1998 | Liedtke | 514/535 |
| 5,981,593 A | * | 11/1999 | Scott | 514/573 |
| 6,054,421 A | * | 4/2000 | Lyons et al. | 508/427 |
| 6,117,877 A | * | 9/2000 | Fogel | 514/23 |
| 6,391,832 B2 | * | 5/2002 | Lyons et al. | 508/427 |

FOREIGN PATENT DOCUMENTS

| WO | WO01/30287 | * | 5/2001 |

* cited by examiner

*Primary Examiner*—Vickie Kim
(74) *Attorney, Agent, or Firm*—Bodner & O'Rourke; Thomas A. O'Rourke

(57) ABSTRACT

The present invention is directed to an improved flowable anesthetic composition that does not need to be applied by an applicator. The anesthetic composition of the present invention may be applied by dripping or spraying the composition onto a wound or other injured area. The composition of the anesthetic includes one or more anesthetics, and a base comprising a surgical lubricant. If desired, the composition may also include one or more vasoconstrictors. The vasoconstrictor is preferably an adrenaline based compound and more preferably epinephrine. The surgical lubricant is preferably water soluble. The anesthetics may include any of the well-known anesthetics such as lidocaine, pontocaine, tetracaine, bupivicaine, procaine and others.

21 Claims, No Drawings

TOPICAL ANESTHETIC

FIELD OF THE INVENTION

The present invention relates to improvements in topical anesthetics and in particular topical anesthetics that may be applied by dripping into a wound or other area without the pressure of an applicator on the wound surface.

BACKGROUND OF THE INVENTION

Many, if not most ailments of the body cause pain or discomfort in some degree. Generally pain is experienced when the free nerve endings which constitute the pain receptors in the skin as well as in certain internal tissues are subjected to mechanical, thermal or chemical stimuli. The pain receptors transmit signals along afferent neurons into the central nervous system and thence to the brain. The causes of pain can include inflammation, injury, disease, muscle spasm and the onset of a neuropathic event or syndrome. Ineffectively treated pain can be devastating to the person experiencing it by limiting function, reducing mobility, complicating sleep, and dramatically interfering with the quality of life.

Inflammatory pain can occur when tissue is damaged, as can result from surgery or due to an adverse physical, chemical or thermal event or to infection by a biologic agent. Although inflammatory pain is generally reversible and subsides when the injured tissue has been repaired or the pain inducing stimulus removed, present methods for treating inflammatory pain have many drawbacks and deficiencies. Neuropathic pain is a persistent or chronic pain syndrome that can result from damage to the nervous system, the peripheral nerves, the dorsal root ganglion or dorsal root, or to the central nervous system. Neuropathic pain syndromes include allodynia, various neuralgias such as post herpetic neuralgia and trigeminal neuralgia, phantom pain, and complex regional pain syndromes, such as reflex sympathetic dystrophy and causalgia. Causalgia is characterized by spontaneous burning pain combined with hyperalgesia and allodynia.

There are many types of anesthetics in use today. One type of anesthetic is a local anesthetic. Local anesthetics act via a loss of sensation in the localized area of administration in the body. The mechanism by which local anesthetics induce their effect, while not having been determined definitively, is generally thought to be based upon the ability to locally interfere with the initiation and transmission of a nerve impulse, e.g., interfering with the initiation and/or propagation of a depolarization wave in a localized area of nerve tissue. The actions of local anesthetics are general, and any tissue where nerve conduction, e.g., cell membrane depolarization occurs can be affected by these drugs. Thus, nervous tissue mediating both sensory and motor functions can be similarly affected by local anesthetics.

Frequently, local anesthetics are administered to the patient by means of an injection. Unfortunately, the injection of the anesthetic can itself be very painful to the individual. Besides the initial insertion of the needle in administering the injection of the anesthetic there are other causes of pain to the patient. For example, the acidity of the anesthetic solution can cause pain. One very common anesthetic lidocaine and others is an acid that burns when it is injected. While this pain can be reduced by, for example, mixing bicarbonate with the injection just before it is given this procedure complicates the treatment of the individual. Another cause of pain from an injection is due to the depth of the injection. Injections into the superficial parts of the skin will hurt more than when injected into the deep layers and beneath the skin. Another factor in causing pain in an injection can be the speed of injection. Injecting as slowly as the needle is removed will also make the pain less.

As a result, there are many instances where an injection is not preferred for administering an anesthetic and the administration of a topical anesthetic is desired. One such instance may be where the pain due to the injection is not desired. Another such instance is in the case of young children. Many children fear an injection sometimes more than the pain they are suffering. As a result, even the sight of a hypodermic needle in an emergency situation can create great discomfort in the patient. As a result, there is a need for a topical anesthetic that may be applied without the use of an injection. In addition, there is a particular need for a topical anesthetic that may be applied to produce a superficial anesthesia that will allow for a painless injection of tissues to produce a deep anesthesia.

One approach to the problem administering anesthetics without an injection is described in U.S. Pat. No. 5,563,153 to Mueller. Mueller discloses a sterile topical anesthetic that employs a product called "GELFOAM®" as the vehicle for the anesthetics of the Mueller composition. GELFOAM® is an absorbable gelatin-based material. The consistency of the Mueller anesthetic is a pasty consistency similar to horseradish or peanut butter. This pasty material once prepared is then applied with an applicator by smearing it over the open wound. The force necessary to apply this paste is rather heavy and the use of the Mueller anesthetic can be very painful and risk further traumitizing an already sensitive injury further.

One of the problems that are encountered with the use of the Mueller composition is that the Mueller formula can inhibit wound healing. This problem stems from the presence of the GELFOAM® in the Mueller composition. The manufacturer of the GELFOAM® product states that the GELFOAM® powder should be made into a doughy paste that can be smeared or pressed against the open wound. The excess should be removed by irrigation prior to closing the wound. Closing over the GELFOAM® may interfere with the healing of the skin edges.

Another issue with respect to the use of GELFOAM® is its stability once formed into a paste. The manufacturer of the GELFOAM® product does not publish stability data on the product once it is removed from the container and formed into a paste. According to the manufacturer the paste must be used immediately. Extemporaneous preparation to avoid the stability issues caused by GELFOAM® would be time consuming and impractical given the need for expediency in the nature of its use. GELFOAM® is also quite expensive. Currently, a single gram of GELFOAM® costs approximately $49.00. Since the Mueller composition requires at least one gram or more of the powder, the use of GELFOAM® would be economically unfeasible in clinical practice due to its high cost.

The Mueller composition has a further infirmity. GELFOAM® has no bacteriostatic agent present. Once exposed to room air, GELFOAM® is an excellent medium for the growth of microbes. The manufacturer of GELFOAM®, however, warns against adding or mixing an antibiotic to the paste to prevent bacterial growth once GELFOAM® has been removed from its sterile container.

There are many types of wounds where the use of an applicator no matter how soft and pliable can create pain or increase the risk of further injury. One such example is eye wounds. The sensitive nature of the ocular tissue makes it very difficult for a topical anesthetic to be applied. Another type of wound that the use of an applicator is not desirable includes wounds to oral mucosa such as canker sores and tooth/gum pain where the slightest pressure of an applicator can cause significant pain to the patient. Those skilled in the art will recognize that there are numerous other types of instances where a topical anesthetic should be administered without the use of an applicator that touches the wound surface.

OBJECTS OF THE INVENTION

It is an object of the invention to provide a topical anesthetic that may be administered without contacting the wound surface with an applicator and causing possible pain.

It is an object of the invention to provide a topical anesthetic that is a fluid that may be dripped onto the surface of a wound.

It is another object of the invention to provide a topical anesthetic of relatively low viscosity such that it can flow over an injured surface.

It is a still further object of the present invention to provide a topical anesthetic that also has bacteriostatic properties.

It is also an object of the present invention to provide a topical anesthetic that does not become unstable over time in storage awaiting use.

It is a further object of the invention to provide a topical anesthetic that is economical to use.

SUMMARY OF THE INVENTION

The present invention is directed to an improved flowable anesthetic composition that does not need to be applied by an applicator. The anesthetic composition of the present invention may be applied by dripping or spraying the composition onto a wound or other injured area. The composition of the anesthetic includes one or more anesthetics, and a base comprising a surgical lubricant. If desired, the composition may also include one or more vasoconstrictors. The vasoconstrictor is preferably an adrenaline based compound and more preferably epinephrine. The surgical lubricant is preferably water soluble. The anesthetics may include any of the well-known anesthetics such as lidocaine, pontocaine, tetracaine, bupivicaine, procaine and others.

In a preferred embodiment, the composition of the present invention may be dripped or sprayed onto a wound and let set for up to about one half hour to anesthesize the wound to a certain depth. At that point a needle may be used to apply more anesthesia but without any pain to the patient.

DETAILED DESCRIPTION OF THE INVENTION

In accordance with the present invention, there is an improved topical anesthetic. This anesthetic has significant advantages over injected anesthetics and also over topical anesthetics that have a GELFOAM® type base. These advantages include a more fluid consistency of the anesthetic of the present invention, which permits the anesthetic to run into or flow onto and adhere to a laceration or other wound site. This less viscous consistency permits the use of the anesthetic in such applications as on oral mucosa for canker and other types of sores as well as tooth and gum pain. The prior art GELFOAM® type anesthetic has a pasty consistency that makes it necessary to use an applicator to apply the anesthetic to a patient. The use of an applicator can result in additional pain for the patent in the administering the anesthetic.

Another significant advantage of the topical anesthetic of the present invention is that it is bacteriostatic and will not support bacterial growth. Consequently, the use anesthetic of the present invention can reduce the risk of infection and can in some instances eliminate a separate application of an antiseptic to a wound. This single step application can reduce treatment time by the caregiver in many instances.

The topical anesthetic composition of the present invention when applied to an open wound, renders the wound insensate after only a short period of time. The anesthetic of the present invention is a mixture of one or more anesthetics, an adrenaline based compound or other vasoconstrictor and a base comprising a surgical lubricant. The anesthetic may be any one or more of those anesthetics known in the art including but not limited to lidocaine, pontocaine, tetracaine, bupivicaine, procaine and others. In a preferred embodiment, the anesthetics are lidocaine HCL, tetracaine HCL, bupivicaine HCL, and the amide and ester moieties of these anesthetics.

The lidocaine component is preferably present in the range of about 2% to about 8% by weight/volume, more preferably 3% to about 7% by weight/volume, and most preferably 4% to about 6% by weight/volume. In one embodiment the composition had about 4% by weight or volume lidocaine.

The tetracaine component is preferably present in the range of about 0.25% to about 1% by weight/volume, more preferably about 0.40% to about 0.75% by weight/volume, and most preferably 0.5% to about 0.6% by weight/volume. In one embodiment the composition had about 0.5% by weight or volume tetracaine.

The bupivicaine component is preferably present tin a range of about 0.5% to about 0.75% by weight/volume.

The procaine component is preferably present in a range of about 5% to about 10% by weight/volume.

In one embodiment of the invention, the composition of the present invention may include a vasoconstrictor such as an adrenalin-based compound. The adrenaline based compound is preferably epinephrine. The adrenaline can be any substance consisting essentially of one or more components from the group consisting of epinephrine, phenylephrine, and norepinephrine. Vasoconstrictors other than an adrenaline component as described herein could be used in place of the adrenaline component. In such instances the amount of the other vasoconstrictor or vasoconstrictors should be similar in amount to the amount of the adrenaline component. Epinephrine is a preferred adrenaline component. The adrenaline based compound is preferably present in a range of about 0.05% to about 1.5% by weight/volume. In one embodiment the composition had about 0.1% by weight or volume of the adrenalin based component.

The vehicle used is preferably but not limited to a water soluble surgical lubricant base known as "Surgilube" or other commercially available surgical lubricants. Surgilube contains water, propylene oxide, chorhexidene gluconate, acetic acid, lavender, propylene glycol, hydroxypropyl, Methyl cellulose, propylene glycol, and sodium acetate. The consistency of this surgical lubricant is that of a free flowing jelly. The surgical lubricant preferably has a bacteriostatic agent present to prevent bacterial growth once removed from its sterile container. One such lubricant is sold by E. Fougera & Co.

One preferred anesthetic composition of the present invention is a mixture of procaine, lidocaine, and epinephrine in a sterile surgical lubricant base. More preferably, the composition of the present invention contains about 5% to 10% by weight of procaine, about 4% lidocaine, about 0.1% epinephrine by weight or volume with the remainder surgical lubricant.

This mixture may be applied to the wound by any suitable means such as by a sterile gauze that has been saturated by the composition. It has been found that the application of the composition of the present invention to patients causes a significant reduction in pain. More specifically, in one test in which the anesthetic composition was copiously applied to patients using a sterile gauze pad for a period of forty-five minute, more than 95% of the patients who were administered the anesthetic reported pain relief.

Another preferred anesthetic composition comprises about 0.5% to about 0.75% bupivicaine, about 4% lidocaine, about 0.1% epinephrine and the remainder a surgical lubricant. The lidocaine is preferably but not limited to that manufactured as an injectable by Abbott Pharmaceutical as a 20% solution. The bupivicaine is preferably but not limited to that manufactured as an injectable by Astra Pharmaceutical. The procaine is preferably but not limited to that manufactured as crystals by Inetgra Chemical Company. The epinephrine is preferably but not limited to a 2% ophthalmic solution sold by Alcon Pharmaceutical. The tetracaine is preferably but not limited to a 2% topical solution sold by Abbott Pharmaceutical.

For example, a 30 ml solution of the preferred formula can be prepared by taking: 6 ml of a 20% lidocaine W/V solution (1.2 gm. lidocaine), 4.5 ml of a 50% procaine W/V solution (2.25 gm. procaine) and 1.5 ml of a 2% epinephrine W/V solution (0.03 gm epinephrine). They are mixed aseptically well to form a uniform solution. This mixture is added to enough Surgilube (i.e. 18 ml) or other surgical lubricant to equal a total volume of 30 ml. This composition is then mixed well until a liquid gel like consistency results. As used herein the term gel is not to be confused with the consistency achieved using a material such as a GELFOAM® type base. A GELFOAM® type base has a thicker consistency and is more viscous. In fact, a GELFOAM® type base typically does not flow as does the gel of the present invention which has a consistency which permits it flow when dripped onto a wound and no pressure is placed on the wound by the application of the anesthetic composition of the present invention. One method of applying the anesthetic composition of the present invention is by means of a dropper. In addition, the composition of the present invention is stable and its constituents do not separate out when the composition is prepared.

Other preferred compositions preferably made as described above include the following:
1) About 0.5% to about 0.75% bupivicane About 0.1% epinephreine About 4% lidocaine QS Surgical lubricant
2) About 5% to about 10% procaine About 0.1% epinephrine About 4% lidocaine QS Surgical lubricant
3) About 0.5% Tetracaine About 0.1% epinephrine About 4% lidocaine QS Surgical lubricant In one embodiment of the present invention, the composition of the present invention may be dripped or sprayed onto a wound and let set for up to about one half hour to anesthesize the wound to a certain depth. At that point a needle may be used to apply more anesthesia but without any pain to the patient.

We claim:

1. A flowable topical anaesthetic composition consisting of one or more anesthetics and a surgical lubricant base consisting of water, propylene oxide, chlorhexidene gluconate, acetic acid, lavender, propylene glycol, methyl cellulose and sodium acetate.

2. The composition according to claim 1 wherein the surgical lubricant is a water soluble base.

3. A flowable topical anaesthetic composition consisting of one or more anesthetics; one or more vasoconstrictors; and a surgical lubricant base consisting of water, propylene oxide, chlorhexidene gluconate, acetic acid, lavender, propylene glycol, methyl cellulose and sodium acetate.

4. The composition according to claim 3 wherein the vasoconstrictor is an adrenaline based compound.

5. The composition according to claim 4 wherein the adrenaline based compound is epinephrine.

6. The composition according to claim 4 wherein the anesthetic is lidocaine.

7. The composition according to claim 4 wherein the anesthetic is tetracaine.

8. The composition according to claim 4 wherein the anesthetic is procaine.

9. The composition according to claim 4 wherein the anesthetic is bupivicane.

10. The composition according to claim 4 wherein the anesthetic is a mixture of bupivicane and lidocaine.

11. The composition according to claim 4 wherein the anesthetic is a mixture of tetracaine and lidoocaine.

12. The composition according to claim 4 wherein the anesthetic is a mixture of procaine and lidocaine.

13. A method of treating a wound comprising applying to said wound a flowable topical anaesthetic composition consisting of one or more anesthetics and a surgical lubricant base consisting of water, propylene oxide, chlorhexidene gluconate, acetic acid, lavender, propylene glycol, methyl cellulose and sodium acetate.

14. The method according to claim 13 wherein said composition is applied by dripping the composition onto the wound.

15. The method according to claim 14 wherein after one half hour, a second application of said composition is applied to said wound.

16. The method according to claim 15 wherein once the composition has anaesthetized the wound more anesthesia may be applied by an applicator without any pain to the patient.

17. The method according to claim 16 wherein said applicator is a needle.

18. The method according to claim 13 wherein said composition is sprayed onto a wound.

19. The method according to claim 18 wherein after one half hour, a second application of said composition is applied to said wound.

20. The method according to claim 19 wherein once the composition has anaesthesized the wound more anesthesia may be applied by an applicator without any pain to the patient.

21. The method according to claim 20 wherein the applicator is a needle.

* * * * *